United States Patent [19]

Teranishi et al.

[11] Patent Number: 4,665,921
[45] Date of Patent: May 19, 1987

[54] HIGH POTENTIAL GENERATING TOOTHBRUSH

[75] Inventors: Akihiko Teranishi, Nagoya; Toshio Fukuoka, Toyoda, both of Japan

[73] Assignee: Teranishi Electric Works, Ltd., Nishikamo, Japan

[21] Appl. No.: 734,653

[22] Filed: May 16, 1985

[30] Foreign Application Priority Data

May 28, 1984 [JP] Japan .................. 59-108063
Oct. 8, 1984 [JP] Japan .................. 59-211175

[51] Int. Cl.$^4$ .............................................. A61N 1/36
[52] U.S. Cl. .................. 128/422; 128/419 R; 128/787; 128/800; 128/801; 604/20
[58] Field of Search ............ 604/20; 128/419 R, 787, 128/800, 801, 803, 804

[56] References Cited

U.S. PATENT DOCUMENTS 3,107,672 10/1963 Hofman ................. 128/801
3,478,741 11/1969 Simon .................. 604/20
4,033,356 7/1977 Hara .................... 128/801

FOREIGN PATENT DOCUMENTS 60452 9/1982 European Pat. Off. .......... 604/20

Primary Examiner—William E. Kamm
Attorney, Agent, or Firm—Oblon, Fisher, Spivak, McClelland & Maier

[57] ABSTRACT

A high potential generating toothbrush including an elongated, manually gripped block handle formed with a positive electrode; a block head formed with a negative electrode and having a brush implanted in one end thereof; and a high voltage generating circuit connected to those positive and negative electrodes for providing a high voltage to both those electrodes and incorporated in either the grip portion or the brush portion. With such construction, it is possible to treat diseases in the oral cavity, and the toothbrush becomes smaller in size and handy.

8 Claims, 13 Drawing Figures

HIGH POTENTIAL GENERATING TOOTHBRUSH

BACKGROUND OF THE INVENTION

(1) Field of Art

The present invention relates to a high potential toothbrush and more particularly to a high potential toothbrush containing a high potential generating circuit and capable of imparting a high negative electrode to a gum portion, etc.

(2) Prior Art

It is known that there may occur an abnormal phenomenon such as an oppressive pain, stiffness, induration or perceptive change in portions on the body surface associated with or corresponding to the portions where there are troubles such as disease, external wound, etc. It will already be well known that such portions on the body surface corresponding to acupunctural point (what is called an effective spot) in such medical field as acupuncture, byssocausis and digital compression. Recently, the technique for measuring a very small potential distributed on the skin surface of the human body or a very small current flowing in the human body has advanced to the extent of making observation of the following phenomenon possible. The skin surface (corneous layer) of the human body usually is negatively charged and the corium side positively charged, but in the event of presence of a trouble such as lesion in the interior of the body, the part (e.g. the foregoing an effective spot) on the body surface corresponding to such abnormal part reverses in electrical polarity. This phenomenon is in short a reflection of an internal trouble to the skin.

On the other hand, based on the knowledge concerning an electric potential of the human body, there has long been conducted a treatment called potential treatment. According to this treatment, a predetermined potential is applied to the human being relative to the earth surface potential on the basis of the following epidemiological finding: "Under an extra-high-tension cable, long-term residents are smaller in the number of those suffering from disease and the growth of crops is better." It has actually been confirmed that in a treating device of a direct current type (imparting a negative electrode to the human body), an equipotential point of constitutional protein in body fluid is varied and the albumin/globulin ratio of the protein is changed according to the polarity of applied potential. It has been considered that such high potential treating device functions to let the foregoing reversal of the skin potential revert to normal to cure the part where a trouble is present.

However, such conventional treating device requires a dedicated high voltage power supply or commercial power supply and special-purpose electrodes, and thus has been difficult to utilize. Inevitably, the treating device itself is large-sized and so the time and place of its use are limited. Besides, in conventional high potential treating devices, since electrode are attached to the surfaces of upper and lower extremities, there arise problems, for example it is impossible to effect treatment in the oral cavity, e.g. treatment through gums.

SUMMARY OF THE DISCLOSURE

It is an object of the present invention to provide a high potential toothbrush as a high potential treating device which is compact, easy to handle and capable of being used in the oral cavity.

It is another object of the present invention to provide a high potential toothbrush which contains a high potential generating circuit and is compact and portable and which therefore can be used any time and anywhere in a repeated manner.

It is a further object of the present invention to provide a high potential toothbrush which gives a good feeling of use and has a uniform distribution of potential in electrodes and which therefore does not cause pain even in the presence of a wound or the like in the oral cavity.

It is a still further object of the present invention to provide a high potential toothbrush capable of strengthening gums and preventing and treating dentoalveolitis.

In order to achieve the above-mentioned objects, the gist of the present invention resides in a high potential toothbrush including a high potential generating circuit A, a positive electrode C of which is formed at a grip portion B, while a positive electrode E thereof is formed at a brush portion D.

DETAILED DESCRIPTION OF PREFERRED EMBODIMENTS

Embodiments of the present invention will be described in detail with reference to the accompanying drawings.

Figure 1:
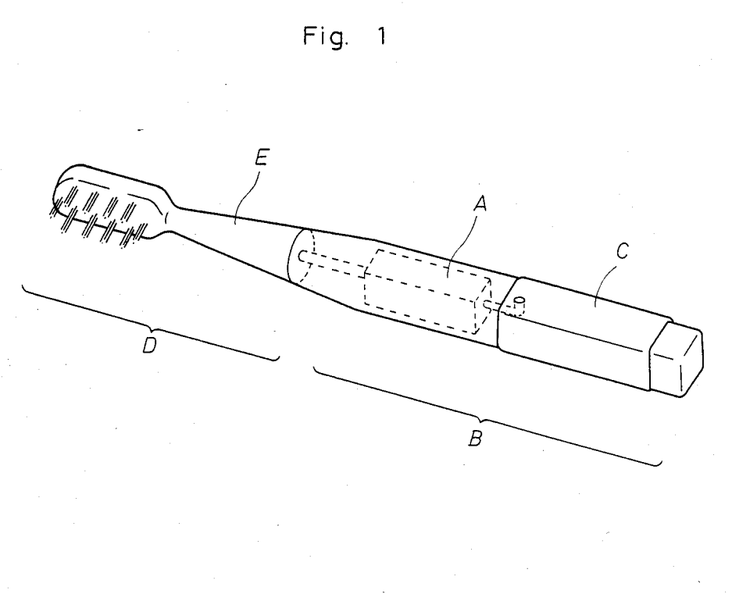
FIG. 1 illustrates a basic construction of the present invention.
Figure 2:
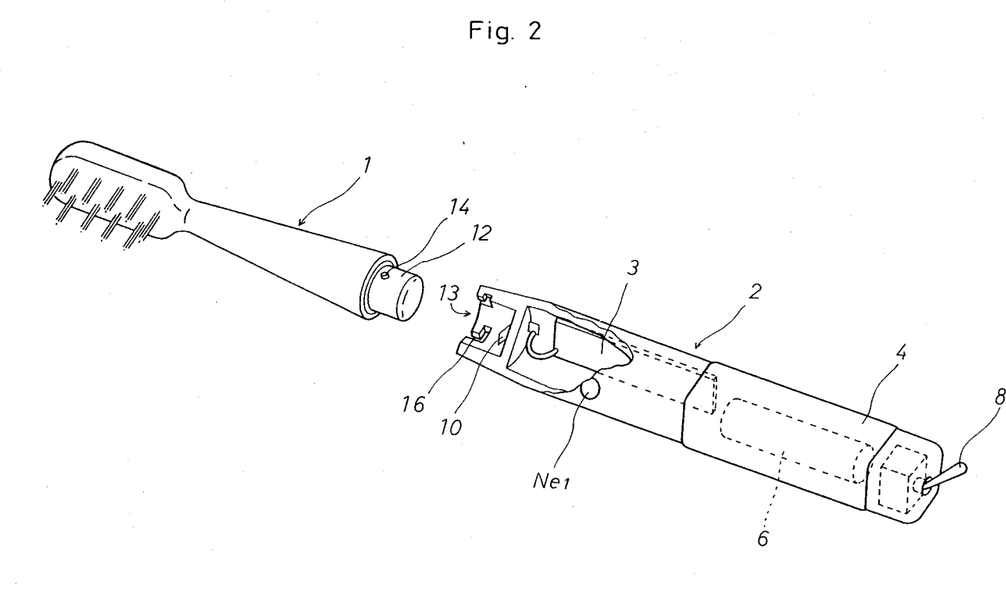
FIG. 2 is a perspective view of a first embodiment of the present invention.

FIG. 1 is a perspective view schematically illustrating a construction of an embodiment of the present invention is an electrical circuit diagram of this embodiment. In these figures, the reference numeral 1 denotes a brush portion formed of an electrically conductive material such as metal, serving per se as an electrode, with nylon bristles implanted in a front portion, and the numeral 2 denotes a grip portion formed of an insulating material and incorporating therein a high voltage generating circuit 3 as a high potential generating circuit, the surface of the grip portion 2 partially covered with an electrically conductive material to form an electrode 4. The brush portion 1 and the grip portion 2 are engageable with and disengageable from each other as will be described later. The numeral 6 denotes a dry cell serving as a power source for the high voltage generating circuit 3; the numeral 8 denotes a switch for turning on and off the power supply of the dry cell 6 for the high voltage generating circuit 3; the numeral 10 denotes a leaf spring-like terminal of the high voltage generating circuit 3; the numeral 12 denotes a convex part adapted to be fitted in a concave part 13 of the grip portion 2 when the brush portion 1 and the grip portion 2 are brought into engagement with each other; the numeral 14 denotes an engaging lug provided at three points on the convex part 12; and the numeral 16 denotes an L-shaped slot formed on the inner peripheral surface of the concave part 13 of the grip portion 12 in positions (three points) corresponding to the lugs 14. The brush portion 1 is integrally fixed to the grip portion 2 by pushing the convex part 12 into the concave part 13 of the grip portion 12 while aligning the lugs 14 with end portions of the L-shaped slots and then turning the brush portion.

Figure 3:
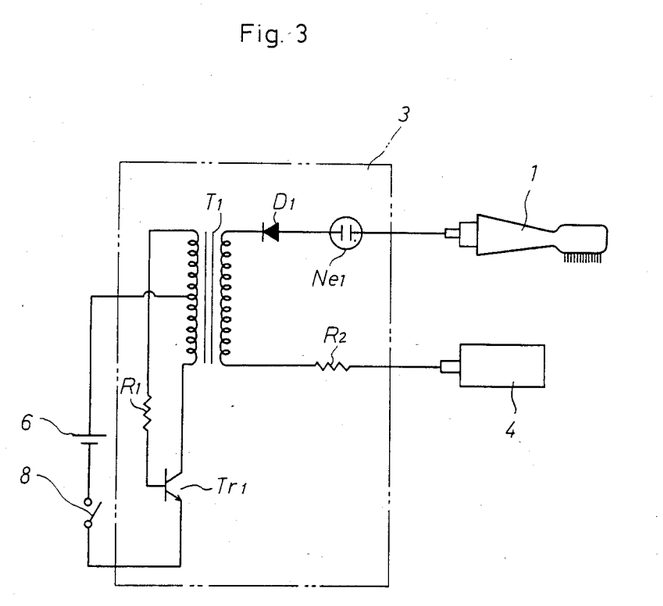
FIG. 3 is an electrical circuit diagram thereof.

Referring now to FIG. 3, there is mainly illustrated the high voltage generating circuit 3 in this embodiment, which is constituted as a so-called free running type blocking oscillator circuit including as principal components an oscillating and boosting transformer $T_1$ and an oscillating transistor $Tr_1$. In the figure, $R_1$ denotes a resistor for limiting the base current of the transistor $Tr_1$; $D_1$ denotes a diode which serves as a rectifying diode in the output circuit of the transistor $T_1$; $Ne_1$ denotes a neon tube which goes on during operation of the high voltage generating circuit 3, thereby permitting a visual confirmation from the exterior; and $R_2$ denotes a protective resistor. The transformer $T_1$ is a secondary transformer having a turn ratio of about 200, in which a plus side of the dry cell 6 is connected to an intermediate tap of a primary coil and one end of the coil is connected to the base of the transistor $Tr_1$ through the resistor $R_1$, while the other end thereof is connected to the collector of the transistor $Tr_1$. When the emitter of the transistor $Tr_1$ is connected to a minus side of the dry cell 6 through a contact of the switch 8, a primary circuit composed of the transformer $T_1$ and the transistor $Tr_1$ oscillates at approximately 2 to 3 kHz to develop a maximum of about 400 volts at the secondary side of the transformer $T_1$. Therefore, when the user takes up the high potential toothbrush, grasps the grip portion 2 and brushes gums, etc., the user's hand inevitably grips the electrode 4, while in the oral cavity the brush portion 1 formed of an electrically conductive material is electrically connected at its bristle-implanted brush 1a with gums, etc. through saliva, etc., so that the high voltage developed at the secondary side of the transformer $T_1$ is applied to the human body. To the secondary closed circuit are connected in series the neon tube $Ne_1$, protective resistor $R_2$ and rectifying diode $D_1$, so even if the human body resistance is decreased to a considerable degree by saliva, etc., there will arise no safety-related problem because there flow a direct current of only about several tens to 200 $\mu A$.

Since this current is rectified by the diode $D_1$, if the electrode 4 of the grip portion 2 is assumed to be a reference potential, it follows that the high potential at the minus side is applied to the gum portion being brushed with the high potential toothbrush. Consequently, the gum portion undergoes such an action as to maintain or return to normal the potential at the skin surface, so it becomes possible to strengthen the gum portion and prevent and treat dentoalveolitis. Moreover, the high potential toothbrush of this embodiment can effect a high potential treatment using a small dry cell 6 as power source without using a commercial power supply, so is employable any time and anywhere. The above effect can be enhanced by a repeated use. In the high potential toothbrush of this embodiment, moreover, since the brush portion 1 is formed of an electrically conductive material and per se serves as an electrode, a simple structure and a superior durability can be attained, and coupled with its disengageable construction with respect to the grip portion 2, it is easy to effect maintenance such as washing and thereby keep the brush portion 1 clean. Additionally, during use of the toothbrush, the neon tube $Ne_1$ goes on according to the current flowing through the secondary side of the transformer $T_1$ and this can be checked visually, so it is possible to easily detect consumption of the dry cell 6.

Figure 4:
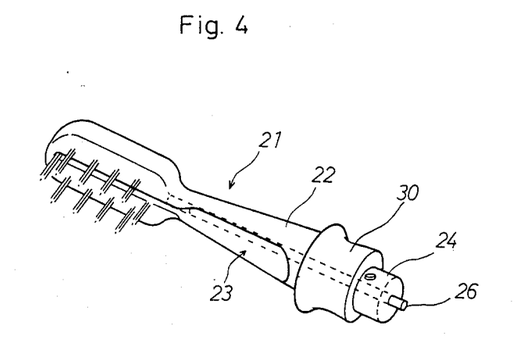
FIG. 4 is a perspective view of a brush portion 21 according to a second embodiment of the invention.
Figure 5:
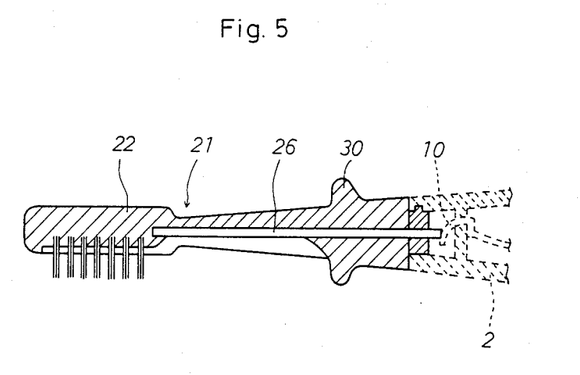
FIG. 5 is a sectional view taken along an axial direction thereof.

A second embodiment of the present invention will now be described with FIGS. 4 and 5, FIG. 4 being a perspective view of a brush portion 51 and FIG. 5a sectional view taken along an axial direction thereof. A grip portion 2 has the same construction as in the first embodiment. The brush portion 21 has a body 22 formed of an insulating material, e.g. a synthetic resin, in which a groove 23 is formed axially toward a bristle-implanted side. Fitted in this groove 23 is a metallic electrode 26 which extends through a convex part 24 for engagement with the grip portion 2. Also in the bristle-implanted area at the front end of the brush portion 21 is formed a slot which is smoothly contiguous to the groove 23. On the other hand, a flange 30 is formed on the engaging side of the body 22 with the grip portion 2. The flange 30 is provided for preventing saliva, etc. from reaching the electrode 4 of the grip portion 2 along the body 22 and causing an electrical connection thereto of the output side of the high voltage generating circuit 3 directly (a kind of short-circuiting) without going through the human body.

In this embodiment constructed as above, there are obtained the following effects in addition to the effects of the first embodiment. In the brush portion 21, the body 22 is formed of an insulating material and a part thereof is grooved axially, in which is disposed the electrode 26. Therefore, as compared with the first embodiment, the entirety can be reduced in weight and a better feeling of use can be attained because the sense of touch in the oral cavity is almost the same as in the use of ordinary toothbrush. Moreover, since the flange 30 is provided on the engaging side of the body 22 with the grip portion 2, saliva, etc. will never reach the grip portion 2, thus avoiding unpleasant feel in use and permitting maintenance of an electrical insulation between both electrodes.

Figure 6:
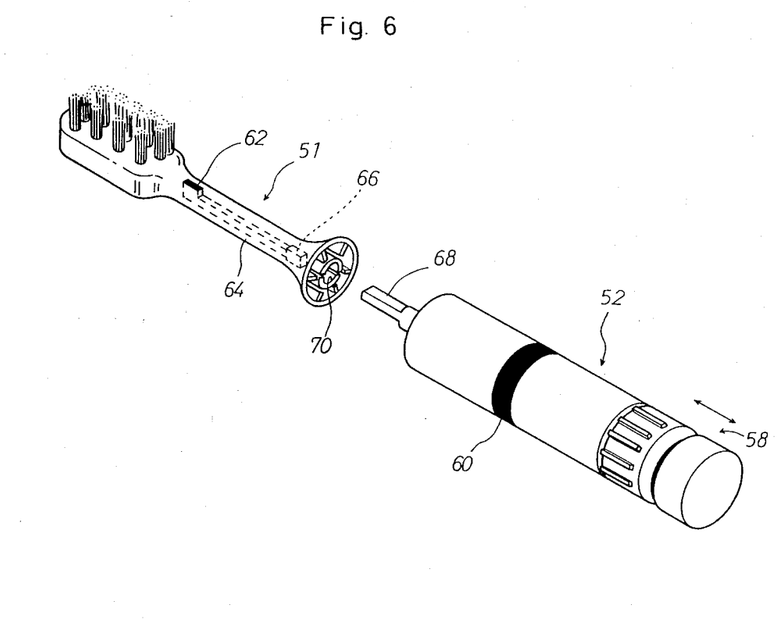
FIG. 6 is a perspective view schematically illustrating a construction of a third embodiment of the invention.
Figure 7:
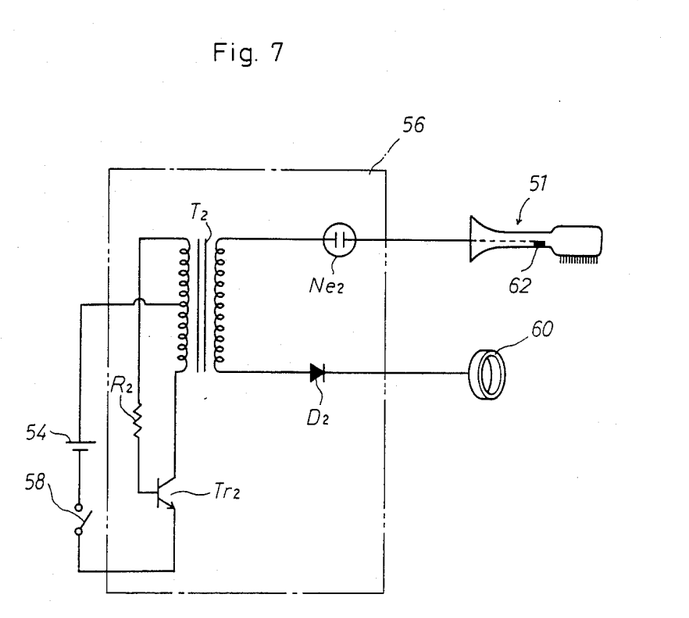
FIG. 7 is an electrical circuit diagram thereof.

A third embodiment of the present invention will now be described with reference to FIGS. 6 and 7. A high potential toothbrush of this embodiment is of a separable structure into a brush portion 51 and a grip portion 52, as shown in FIG. 6. The grip portion 52 incorporates a dry cell 54 and a high voltage generating circuit 56 having such a construction as shown in FIG. 7. The circuit 56 is constructed so as to produce a high voltage upon turning on the switch 58. To facilitate operation, the switch 58 is provided in such a form that the whole of a tail part of the grip portion 52 is allowed to slide. Being drawn out, the switch 58 is turned on. The high voltage generating circuit 56 consists basically of a Colpitts oscillator circuit similar to the first embodiment and it is configured as shown in FIG. 7 from transistor Tr$_2$, transformer T$_2$, resistor R$_2$, neon tube Ne$_2$ and diode D$_2$.

The grip portion 52 is provided with a ring-like stainless steel electrode 60, while in the brush portion 51 an electrode 62 is exposed rectangularly at the base of the bristle-implanted portion. The electrode 62, formed of an L-shaped stainless steel, is embedded in a shaft 64 of the brush portion 51, with one end in contact with an electrically conductive rubber 66. As the brush portion 51 is brought into engagement with the grip portion 52, an electrically conductive material 68 made of stainless steel and projecting from an engaging surface of the grip portion 52 with the brush portion 51 is inserted in a fitting hole 70 of the brush portion 51. At this time, through an engaging mechanism (not shown) attached to the conductive material 68, the fore end of the conductive material 68 is brought into pressure engagement with the conductive rubber 66.

Therefore, the conductive material 68 is connected to a minus output terminal of the high voltage generating circuit 56, so if in this state the switch 58 is drawn out and turned on, the electrode 62 of the brush portion 51 assumes a minus potential. Thus, if the user grasps the grip portion 52 and brushes gums, etc., there will be obtained the same effects as in the first and second embodiments. In this embodiment, moreover, since the electrode 62 is exposed only at the root of the bristle-implanted portion, a high electric field distribution is developed only at and near the gum portion in the oral cavity. As a result, a high potential can be applied efficiently to the gum portion, and since the current flowing in a specific part becomes large, such an action as, for example, removing tartar is created to some extent. Further, since the electrode 62 is exposed smoothly to the surface of the brush portion 51, there will stay no fur or residue after teeth brushing, whereby the toothbrush can be easily kept clean.

In the embodiments described above, an ordinary dry cell is used as a power source and a high voltage is taken out through a free running type oscillator circuit and a boosting transformer. However, any boosting circuit may be used. For example, a multilayer lithium dry cell capable of generating a high voltage may be used directly as a high voltage generating circuit. Further, the dry cell 6 may be substituted by a chargeable cell capable of being charged from a commercial power supply. Moreover, although in the above embodiments, the brush portion 1, 21 or 51 and the grip portion 2 or 52 are made disengageable from each other, both portions may be formed integrally to simplify construction and thereby reduce the manufacturing cost. Further, although in the above embodiments an electrically conductive material (e.g. metal) is used as the electrode of the brush portion and bristles are separately implanted to serve as a brush, bristles formed of a material superior in electric conductivity such as, for example, carbon fibers may be implanted in a fore end part of the brush portion directly as an electrode.

Figure 8:
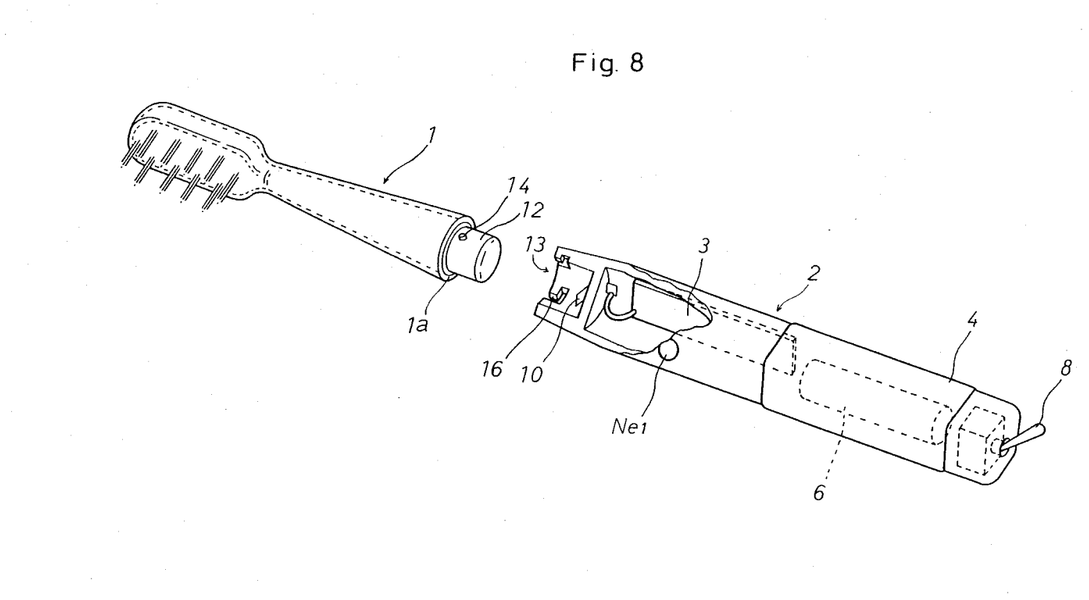
FIG. 8 is a perspective view of a fourth embodiment of the invention.
Figure 9:
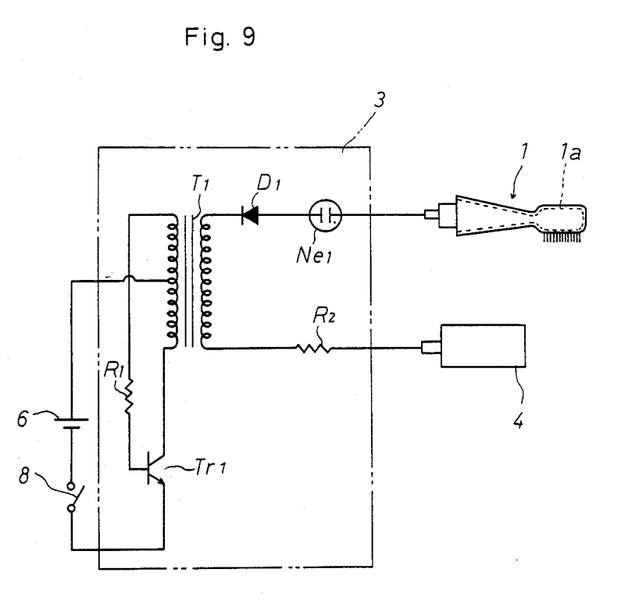
FIG. 9 is an electrical circuit diagram thereof.

Referring now to FIGS. 8 and 9, there is illustrated a fourth embodiment of the present invention, FIG. 8 and FIG. 9 shows a perspective view and an electrical circuit diagram. In these figures, the reference numeral 1 denotes a brush portion formed of an electrically conductive material such as metal as a negative electrode and covered on its surface with a coating 1a of a soft plastic material such as polypropylene, with nylon bristles implanted in the front end. The other components are of the same construction as in the first embodiment. Operation is also about the same as in the first embodiment, but since the brush portion 1 formed of a conductive material and covered with the insulating coating 1a comes close to gums in the oral cavity, voltage is developed on the secondary side of the transformer T$_1$ and a negative electrode distributed in the brush portion 1 is imparted to the gums, etc.

In the high potential toothbrush of this embodiment, moreover, since the negative electrode is covered with the polypropylene coating 1a, the distribution of potential becomes uniform and a wound or the like if any in the oral cavity would not cause pain. Moreover, the feeling of use is good without feeling of a foreign substance because the coating 1a touches the skin softly.

Figure 10:
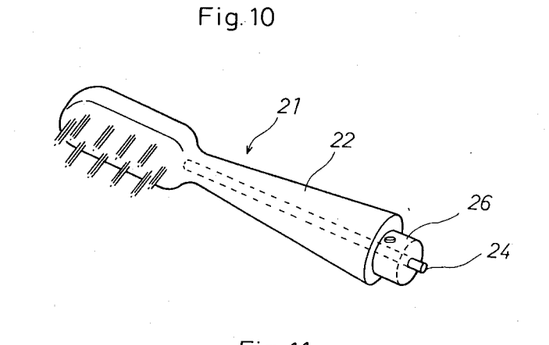
FIG. 10 is a perspective view of a brush portion 21 according to a fifth embodiment of the invention.
Figure 11:
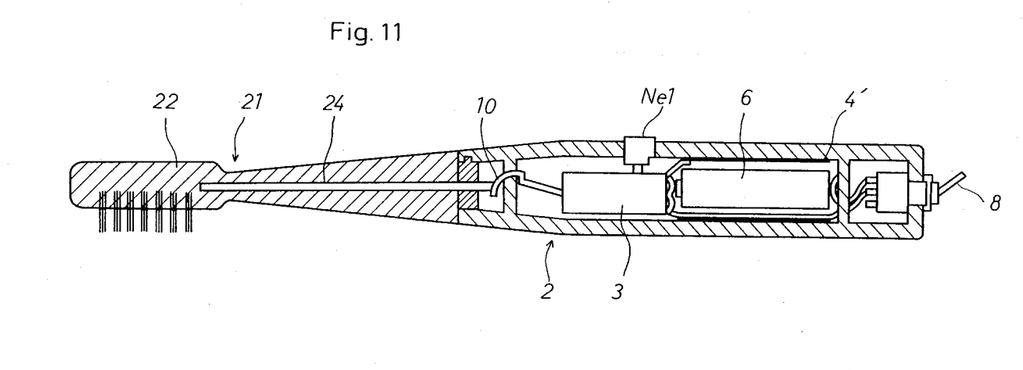
FIG. 11 is a sectional view taken along an axial direction of a high potential toothbrush of the fifth embodiment.

A fifth embodiment of the present invention will be described below with reference to FIGS. 10 and 11. FIG. 10 is a perspective view of a brush portion 21 and FIG. 11 is a sectional view taken along an axial direction, schematically showing a construction of the whole of a high potential toothbrush, including a grip portion.

In this embodiment, the brush portion 21 has a body 22 formed of an insulating material, e.g. a synthetic resin, with bristles implanted in its front end. The brush 21 is molded with a metallic negative electrode 24 in such a manner that the electrode is inserted through an engaging convex part 26. One end of the negative electrode 24 extends toward a grip portion 2 so as to be brought into pressure contact with a leaf spring-like terminal 10 for connection with a high voltage generating circuit 3.

On the other hand, the construction of the grip portions is the same as in the first embodiment except a positive electrode 4'. Unlike the first embodiment in which the electrode 4 is formed outside the grip portion 2, the positive electrode 4' in this embodiment is in close contact with the inner wall of the grip portion 2, that is, the electrode 4 is covered with an insulating material such as plastic material which forms the body of the grip portion 2.

In this embodiment constructed as above, there are obtained the following effects in addition to the effects of the fourth embodiment. In the brush portion 21, since the negative electrode 24 is inserted axially through the body 22 formed of an insulating material, it is possible to reduce the entire weight as compared with the fourth embodiment, and since the sense of touch in grasping the toothbrush and that in the oral cavity are almost the same as in ordinary toothbrushes, a better feeling of use can be obtained.

Figure 12:
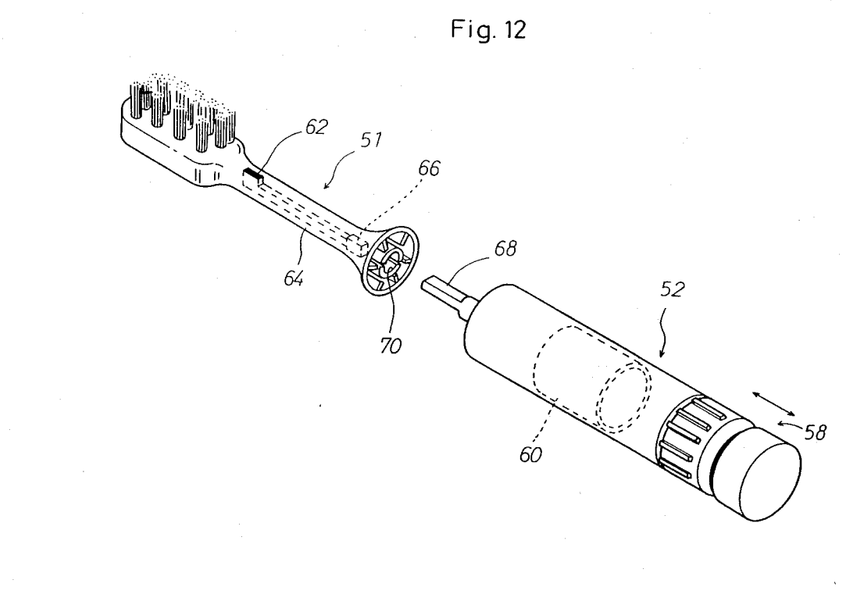
FIG. 12 is a perspective view schematically illustrating a construction of a sixth embodiment of the invention.
Figure 13:
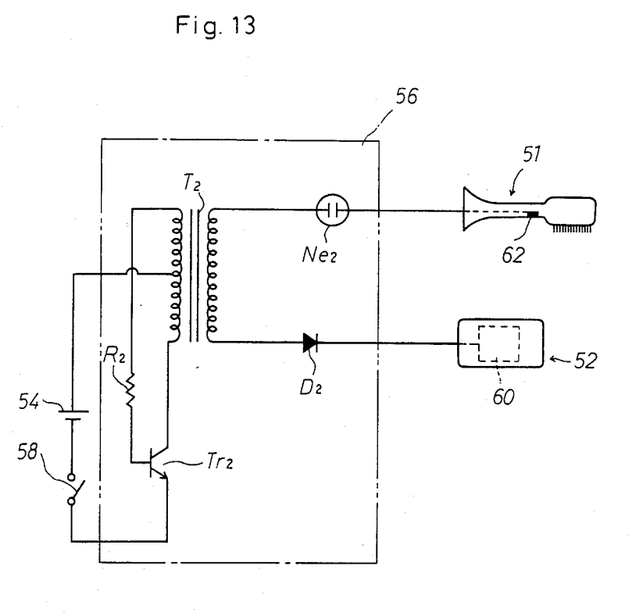
FIG. 13 is an electrical circuit diagram thereof.

Referring now to FIGS. 12 and 13, there is illustrated a sixth embodiment of the present invention, in which a high potential toothbrush is of a separable structure into a brush portion 51 and a grip portion 52, as shown in FIG. 12, and an electrode 60 is provided in the form of a ring covered with an synthetic resin which forms the body of the grip portion 52. In the grip portion 52 are incorporated a dry cell 54 and a high voltage generating circuit 56 of such a construction as shown in FIG. 13. The circuit 56 is so constructed as to produce a high voltage upon turning on of a switch 58. To facilitate operation, the switch 58 is provided in such a form that the whole of a tail part of the grip portion 52 is allowed to slide. When drawn out, the switch 58 is turned on. The high voltage generating circuit 56 consists basically of a Colpitts oscillator circuit similar to the fourth embodiment and it is formed as shown in FIG. 13 from transistor $Tr_2$, transformer $T_2$, resistor $R_2$, neon tube $Ne_2$ and diode $D_2$.

Several embodiments of the present invention have been described above, but it is to be understood that the invention is not limited thereto and that various modifications may be made within the scope not departing from the gist of the invention.

What is claimed is:

1. A high potential generating toothbrush comprising:
   an elongated, manually gripped block handle;
   a positive electrode formed at said block handle;
   a block head with bristles implanted in one end;
   a negative electrode formed at said block head; and
   a high voltage generating means connected to said positive electrode and said negative electrode for providing a high voltage to both of said electrodes.

2. A high potential generating toothbrush as set forth in claim 1, wherein at least a part near the implanted bristles of said block head is grooved and said negative electrode is formed in said groove.

3. A high potential generating toothbrush as set forth in claim 1, further comprising an insulating material covering at least one of said positive and negative electrodes.

4. A high potential generating toothbrush as set forth in claim 3, wherein said insulating material is a synthetic resin.

5. A high potential generating toothbrush as set forth in claim 1, wherein said high voltage generating means is incorporated in said block handle and wherein said block head and said block handle have means engageable with and disengageable from each other.

6. A high potential generating toothbrush as set forth in claim 5, wherein said positive electrode is in the shape of a ring, said negative electrode is linear, and wherein said positive and negative electrodes are made of stainless steel.

7. A high potential generating toothbrush as set forth in claim 1, wherein said high potential generating means comprises a direct current power source and a means for boosting the electrical potential of said direct current source.

8. A high potential generating toothbrush as set forth in claim 7, further comprising a switch means for controlling operation of said high voltage generating means in an on-off manner,
   said means for boosting the potential of the source including a free running type oscillator which oscillates at 2-3 kHz and produces a voltage of a maximum of about 400 volts.

* * * * *